United States Patent [19]

Rueb et al.

[11] Patent Number: 4,888,046
[45] Date of Patent: Dec. 19, 1989

[54] N-PHENYLTETRAHYDROPHTHALIMIDE COMPOUNDS

[75] Inventors: Lothar Rueb, Speyer; Karl Eicken, Wachenheim; Bernd Zeeh, Limburgerhof; Norbert Meyer, Ladenburg; Bruno Wuerzer, Otterstadt, all of Fed. Rep. of Germany

[73] Assignee: BASF Aktiengesellschaft, Ludwigshafen, Fed. Rep. of Germany

[21] Appl. No.: 263,352

[22] Filed: Oct. 27, 1988

[30] Foreign Application Priority Data

Oct. 27, 1987 [DE] Fed. Rep. of Germany ....... 3736297

[51] Int. Cl.⁴ .................. A01N 43/38; C07D 307/12; C07D 333/16
[52] U.S. Cl. .......................... 71/90; 71/96; 548/465
[58] Field of Search ........................ 548/465; 71/96, 90

[56] References Cited

U.S. PATENT DOCUMENTS 4,292,070  9/1981  Wakabayashi et al. ................ 71/96

FOREIGN PATENT DOCUMENTS 59-082360 12/1984 Japan ..................................... 548/465
87-07602 12/1987 PCT Int'l Appl. ................. 548/513

Primary Examiner—Mary E. Ceperley
Attorney, Agent, or Firm—Oblon, Spivak, McClelland, Maier & Neustadt

[57] ABSTRACT

N-Phenyltetrahydrophthalimide compounds of the formula I

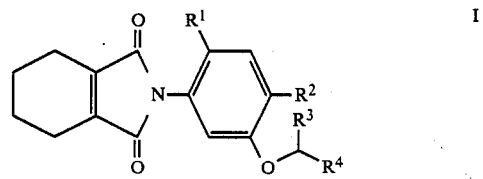

where $R^1$ is hydrogen, fluorine or chlorine, $R^2$ is chlorine or bromine, $R^3$ is hydrogen or $C_1$–$C_3$-alkyl, and $R^4$ is a 5- or 6-membered, saturated or unsaturated heterocyclic compound containing an oxygen or a sulfur atom and which is unsubstituted or substituted by a maximum of three $C_1$–$C_3$-alkyl groups, methods of manufacturing these compounds, and their use as herbicides.

3 Claims, No Drawings

N-PHENYLTETRAHYDROPHTHALIMIDE COMPOUNDS

The present invention relates to N-phenyltetrahydrophthalimide compounds of the formula I

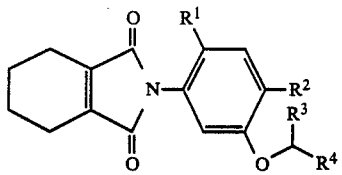

where $R^1$ is hydrogen, fluorine or chlorine, $R^2$ is chlorine or bromine, $R^3$ is hydrogen or $C_1$–$C_3$-alkyl and $R^4$ is a 5-membered or 6-membered saturated or unsaturated heterocyclic structure which contains an oxygen or sulfur atom in the ring and may be substituted by up to three $C_1$–$C_3$-alkyl groups.

The present invention furthermore relates to a process for the preparation of the compounds I and their use as herbicides.

The literature discloses N-aryl-substituted tetrahydrophthalimides having a herbicidal action. For example, DE-A 3 013 162 describes tetrahydrophthalimides whose activity is unsatisfactory at low application rates.

It is an object of the present invention to synthesize compounds which have higher selectivity with respect to crops at relatively low application rates.

We have found that this object is achieved by the N-tetrahydrophthalimide compounds I, which have an advantageous herbicidal action, particularly in the post-emergence method, and are selective with regard to a number of crops.

In specific cases and in the case of some crops, the compounds I are also suitable as dessicants for killing the green shoots to facilitate harvesting.

N-phenyltetrahydrophthalimide compounds of the formula I can be obtained, for example, by reacting an appropriately substituted N-(3-hydroxyphenyl)-3,4,5,6-tetrahydrophthalimide II with a suitable compound of the formula III at up to 200° C., preferably from 25° to 150° C., in a suitable solvent in the presence of a base.

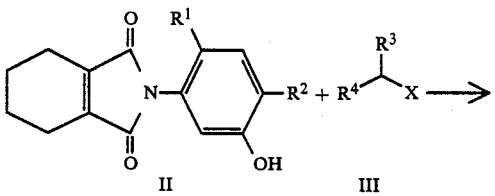

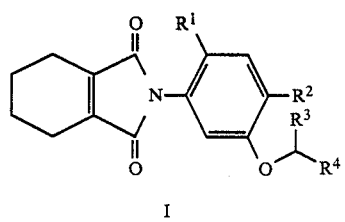

In formula III, X is halogen, eg. chlorine, bromine or iodine, or sulfonyloxy, eg. methylsulfonyloxy, trifluoromethylsulfonyloxy, phenylsulfonyloxy or tolylsulfonyloxy, preferably bromine or tolylsulfonyloxy.

The N-phenyltetrahydrophthalimide compounds of the formula I are also obtained, for example, by reacting 3,4,5,6-tetrahydrophthalic anhydride with an appropriate aniline IV, for example in a solvent at up to 200° C., preferably from 40° to 150° C.

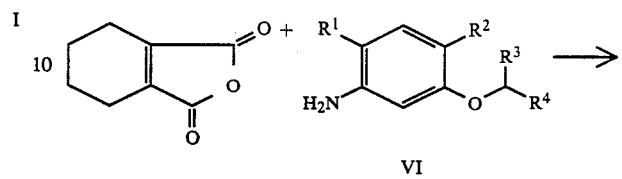

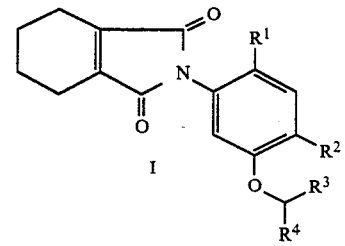

Examples of suitable solvents are lower alkanoic acids, such as glacial acetic acid or propionic acid, or aprotic solvents, such as toluene or xylene, in the presence of acidic catalysts, such as aromatic sulfonic acids.

The aniline derivatives VI can be obtained, for example, by hydrogenating an appropriately substituted nitro compound V in the presence of Raney nickel or of a noble metal catalyst, such as platinum or palladium, or by reducing the said nitro compound by means of a reducing agent, such as iron or a tin(II) salt.

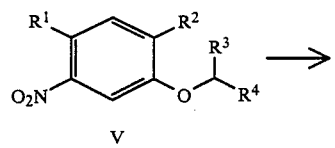

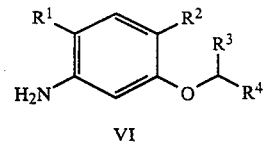

The nitro compounds V are obtainable by reacting an appropriate phenol IV with a compound of the formula III at up to 200° C., preferably from 25° to 150° C., in an aprotic polar solvent (eg. acetone, acetonitrile or dimethylformamide), in the presence of a base (eg. potassium carbonate, sodium hydroxide or sodium hydride).

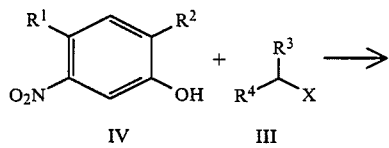

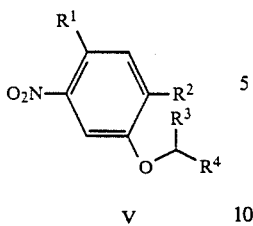

R¹ is preferably hydrogen or fluorine and R² is preferably chlorine.

The term alkyl includes branched and straight-chain radicals, ie. methyl, ethyl, n-propyl and isopropyl.

The 5-membered and 6-membered heterocyclic structures of the formula I are hydrogenated or partially hydrogenated furan, thiophene, pyran and thiopyran derivatives, preferably tetrahydrofuran, tetrahydrothiophene, tetrahydropyran, dihydropyran, tetrahydrothiopyran or dihydrohydropyran. If they are polysubstituted, all possible stearic arrangements may occur. These may have different biological effects.

Preferred compounds I are those in which R¹ is hydrogen or fluorine, R² is chlorine, R³ is hydrogen and R⁴ is 2- or 3-tetrahydrofuranyl, 2- or 3-tetrahydrothienyl, 2-, 3- or 4-tetrahydropyranyl, 2-, 3- or 4-tetrahydrothiopyranyl, 5,6-dihydro-2H-pyranyl or 5,6-dihydro-2H-thiopyranyl.

The recommended procedures stated in the Examples below were used to obtain further compounds of the general formula I, with appropriate modification of the starting compounds. The compounds are listed together with physical data in the Table below. Compounds without such data can be obtained from corresponding substances in a similar manner. Because of their close structural relationship with the compounds prepared and investigated, they are expected to have a similar action.

EXAMPLE 1 (PROCESS A)

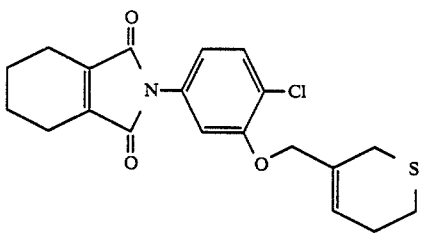

13.9 g of N-(4-chloro-3-hydroxyphenyl)-3,4,5,6-tetrahydrophthalimide, 8.2 g of 3-chloromethyl-5,6-dihydro-2H-thiopyran and 8.3 g of potassium carbonate in 150 ml of acetonitrile were refluxed for 5 hours. After cooling, the mixture was filtered, the filtrate was evaporated down, the residue was taken up in 200 ml of methylene chloride and the solution was washed twice with 10% strength sodium hydroxide solution and three times with water, dried and evaporated down. 15.0 g of N-[4-chloro-3-(3-methoxy-5,6-dihydro-2H-thiopyranyl-3-methyloxy)-phenyl]-3,4,5,6-tetrahydrophthalimide (mp. 116°-119° C.) were obtained (Table 1, No. 9)

EXAMPLE 2 (PROCESS B)

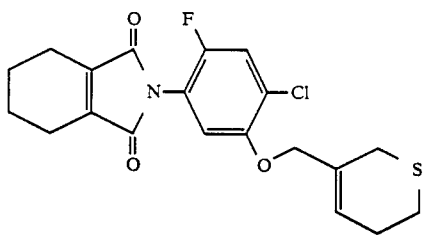

(a) 9.6 g of 1-chloro-4-fluoro-5-nitrophenol, 8.2 g of 3-chloromethyl-5,6-dihydro-2H-thiopyran and 3.8 g of potassium carbonate in 150 ml of acetonitrile were refluxed for 5 hours. The mixture was cooled and filtered, the filtrate was then evaporated down and the residue was taken up in 200 ml of methylene chloride. The organic phase was washed with three times 50 ml of water, dried and evaporated down and the residue was stirred with petroleum ether. 12.5 g of 2-chloro-4-fluoro-5-nitro-(5,6-dihydro-2H-thiopyran-3-ylmethoxy)-benzene were obtained (mp. 91°-94° C.).

(b) 12.2 g of the above nitro compound were added a little at a time to a refluxed mixture of 6.7 g of iron powder in 50 ml of methanol and 7.5 ml of glacial acetic acid, and refluxing was continued for 2 hours. After the mixture had cooled, 250 ml of water were added and the mixture was filtered under suction. The filtrate was extracted with three times 100 ml of ethyl acetate, the extract was dried and the solvent was evaporated off under reduced pressure. Purification by chromatography gave 5.5 g of 4-chloro-2-fluoro-5-(5,6-dihydro-2H-thiopyran-3-ylmethoxy)-aniline (mp. 73°-74° C.).

(c) 5.5 g of the above aniline and 3.0 g of cyclohexene-1,2-dicarboxylic anhydride in 100 ml of glacial acetic acid were refluxed for 5 hours. After the mixture was cooled, 50 ml of water were added and the precipitate was filtered off, washed with water and dried. 6.0 g of N-[4-chloro-2-fluoro-5-(5,6-dihydro-2H-thiopyran-3-ylmethoxy)-phenyl]-3,4,5,6-tetrahydrophthalimide (mp. 134°-137° C.) were obtained (Table 1, No. 10).

Further Examples of active ingredients which can be prepared by these synthesis principles are shown in Table 1.

TABLE 1

| No. | R¹ | R² | R³ | R⁴ | mp (°C.) |
|---|---|---|---|---|---|
| 1 | H | Cl | H | tetrahydrothiopyranyl | |
| 2 | F | Cl | H | tetrahydrothiopyranyl | |

TABLE 1-continued
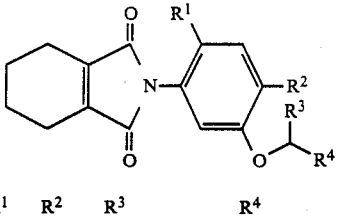
| No. | R¹ | R² | R³ | R⁴ | mp (°C.) |
|---|---|---|---|---|---|
| 3 | H | Cl | H | 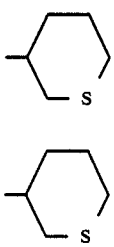 | 143-146 |
| 4 | F | Cl | H | 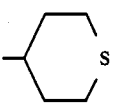 | 162-164 |
| 5 | H | Cl | H | 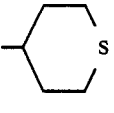 | |
| 6 | F | Cl | H | 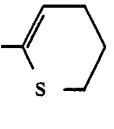 | |
| 7 | H | Cl | H | 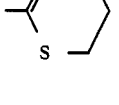 | |
| 8 | F | Cl | H | 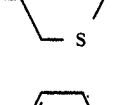 | |
| 9 | H | Cl | H | 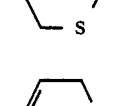 | 116-119 |
| 10 | F | Cl | H | 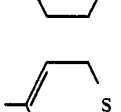 | 134-137 |
| 11 | H | Cl | H | 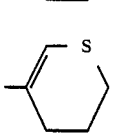 | |
| 12 | F | Cl | H |  | |
| 13 | H | Cl | H | 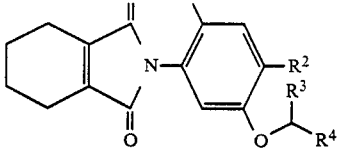 | |
| 14 | F | Cl | H | 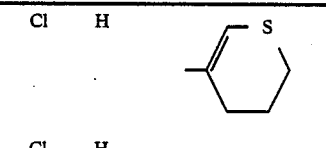 | |
| 15 | H | Cl | H | 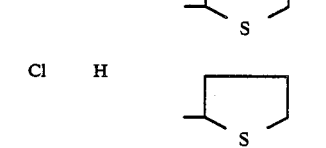 | |
| 16 | F | Cl | H | 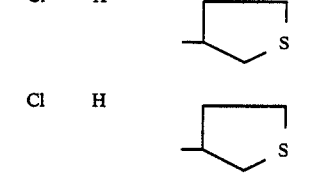 | |
| 17 | H | Cl | H | 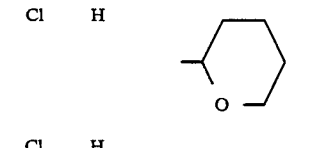 | |
| 18 | F | Cl | H | 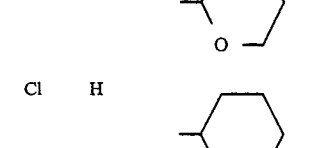 | |
| 19 | H | Cl | H | 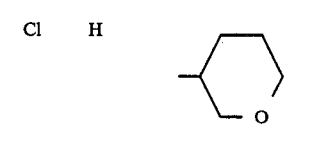 | |
| 20 | F | Cl | H | 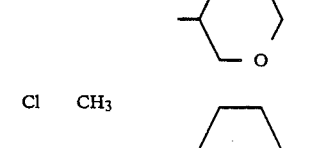 | |
| 21 | H | Cl | H | 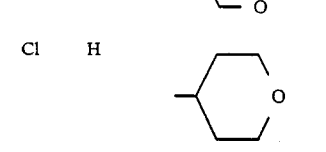 | 108-110 |
| 22 | F | Cl | H |  | 104-106 |
| 23 | H | Cl | CH₃ |  | |
| 24 | F | Cl | CH₃ |  | |
| 25 | H | Cl | H |  | 140-141 |

TABLE 1-continued

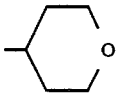

| No. | R¹ | R² | R³ | R⁴ | mp (°C.) |
|---|---|---|---|---|---|
| 26 | F | Cl | H | 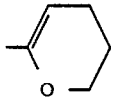 | |
| 27 | H | Cl | H | 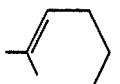 | |
| 28 | F | Cl | H | 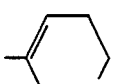 | |
| 29 | H | Cl | H | 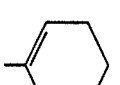 | 90–92 |
| 30 | F | Cl | H | 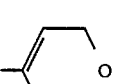 | 131–133 |
| 31 | H | Cl | H | 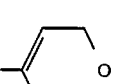 | |
| 32 | F | Cl | H | 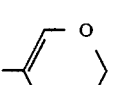 | |
| 33 | H | Cl | H | 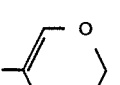 | |
| 34 | F | Cl | H | 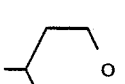 | |
| 35 | H | Cl | H | 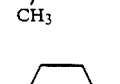 | |
| 36 | F | Cl | H | 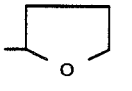 | |
| 37 | H | Cl | H | 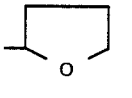 | 74–76 |
| 38 | F | Cl | H | 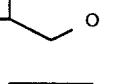 | |
| 39 | H | Cl | H | 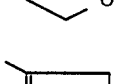 | |
| 40 | F | Cl | H | 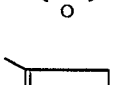 | |
| 41 | H | Cl | H | 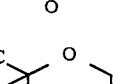 | |
| 42 | F | Cl | H | 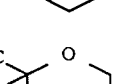 | |
| 43 | H | Cl | CH₃ | 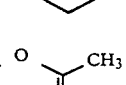 | |
| 44 | F | Cl | CH₃ | 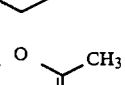 | |
| 45 | H | Cl | CH₃ |  | |
| 46 | F | Cl | CH₃ | 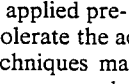 | |

The herbicidal agents, or the active ingredients (I) on which they are based, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.005 to 3.0, preferably 0.01 to 0.5, kg/ha.

The action of the active ingredients of the formula I on the growth of plants is illustrated in greenhouse experiments.

The vessels employed were plastic flowerpots having a volume of 300 cm$^3$ and filled with a sandy loam containing about 3.0% humus. The seeds of the test plants were sown separately, according to species.

For the postemergence treatment, either plants which had been sown in the pots and grown there were selected, or they were cultivated separately as seedlings and transplanted to the pots a few days before being treated.

Depending on growth form, the plants were grown to a height of from 3 to 15 cm before being treated with the active ingredients which were suspended or emulsified in water and sprayed through finely distributing nozzles. The application rates for postemergence treatment varied from 0.015 to 0.125 kg/ha.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments belonged to the following species:

| Abbreviation | Botanical name | Common name |
|---|---|---|
| ABUTH | Abutilon theophrasti | velvet leaf |
| AMARE | Amaranthus spp. | pigweed |
| CHEAL | Chenopodium album | lambsquarters |
| CHYCO | Chrysanthemum coronar. | marigold |
| GALAP | Galium aparine | catchweed bedstraw |
| IPOSS | Ipomoea spp. | morningglory |
| LAMAM | Lamium amplexicaule | henbit |
| MERAN | Mercurialis annua | annual mercury |
| POLPE | Polygonum persicaria | ladysthumb |
| SOLNI | Solanum nigrum | black nightshade |
| STEME | Stellaria media | chickweed |
| TRZAS | Triticum aestivum | wheat |
| TRZAW | Triticum aestivum | wheat |
| VERSS | Veronica spp. | speedwell |
| VIOAR | Viola arvensis | violet |

Compounds 29, 9, 3 and 10 have, on postemergence application, a good herbicidal action on unwanted broadleaved plants at low dosage rates (Table 2).

Unwanted broadleaved plants are successfully combated by novel active ingredients 21, 22 and 4 at postemergence rates of 0.03 and 0.06 kg/ha. Wheat suffers at most slight and temporal damage which disappears on further growth; these herbicides are selective (Tables 3 and 4).

In view of the number of application methods available the compounds according to the invention, or agents containing them, may be used in a further large number of crop plants for combating unwanted plants. Examples of such crops are as follows:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |

| Botanical name | Common name |
|---|---|
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize |

To increase the spectrum of action and to achieve synergistic effects, the active ingredients of the formula I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, cyclohexenones, (hetero)-aryloxy-phenoxypropionic acid and salts, esters and amides thereof, etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE 2

Herbicidal action on the growth of unwanted plants; postemergence application in the greenhouse

| Ex. no. | $R^1$ | $R^3$ | $R^4$ | kg/ha | ABUTH | AMARE | MERAN | SOLNI |
|---|---|---|---|---|---|---|---|---|
| 29 | H | H |  | 0.06 | 100 | 100 | 100 | 100 |
| 9 | H | H |  | 0.125 | 100 | 100 | 100 | 100 |
| 3 | H | H |  | 0.06 | 100 | 100 | 100 | 100 |
| 10 | F | H |  | 0.015 | 100 | 100 | 100 | 100 |

TABLE 3

Herbicidal action on unwanted plants and tolerance by a selected crop; postemergence application in the greenhouse

| Ex. no. | $R^1$ | $R^3$ | $R^4$ | kg/ha | TRZAS | AMARE | GALAP | IPOSS | STEME | VIOAR |
|---|---|---|---|---|---|---|---|---|---|---|
| 21 | H | H | | 0.03 | 10 | 100 | 95 | 95 | 95 | 95 |

TABLE 3-continued

Herbicidal action on unwanted plants and tolerance by a selected crop; postemergence application in the greenhouse

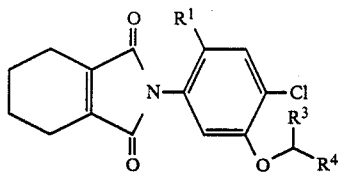

| Ex. no. | $R^1$ | $R^3$ | $R^4$ | kg/ha | TRZAS | AMARE | GALAP | IPOSS | STEME | VIOAR |
|---|---|---|---|---|---|---|---|---|---|---|
| 22 | F | H | | 0.06 | 10 | 100 | 98 | 100 | 100 | 100 |

TABLE 4

Herbicidal action on unwanted plants and tolerance by a selected crop; postemergence application in the greenhouse

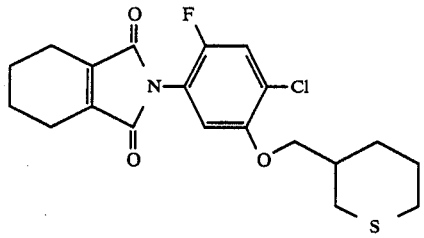

| Ex. no. | kg/ha | TRZAW | CHEAL | CHYCO | IPOSS | LAMAM | POLPE | VERSS |
|---|---|---|---|---|---|---|---|---|
| 4 | 0.03 | 0 | 100 | 100 | 100 | 98 | 100 | 100 |

We claim:
1. An N-phenyltetrahydrophthalimide compound of the formula I

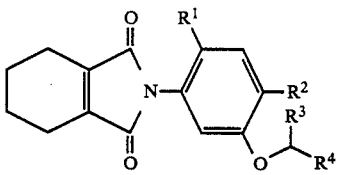

where $R^1$ is hydrogen, fluorine or chlorine, $R^2$ is chlorine or bromine, $R^3$ is hydrogen or $C_1$-$C_3$-alkyl, and $R^4$ is a 5- or 6-membered, saturated or unsaturated heterocyclic compound containing an oxygen or a sulfur atom and which is unsubstituted or substituted by a maximum of three $C_1$-$C_3$-alkyl groups.

2. A process for combating the growth of unwanted plants, wherein a herbicidally effective amount of a compound I as set forth in claim 1 is used.

3. A herbicidally effective agent containing a herbicidally effective amount of a compound I as set forth in claim 1 and conventional auxiliaries, extenders or diluents.

* * * * *